United States Patent [19]
Kane et al.

[11] Patent Number: 4,912,095
[45] Date of Patent: Mar. 27, 1990

[54] 5-ARYL-2,4-DIALKYL-3H-1,2,4-TRIAZOLE-3-THIONES USEFUL AS ANTIDEPRESSANTS

[75] Inventors: John M. Kane, Cincinnati; Francis P. Miller, Loveland, both of Ohio

[73] Assignee: Merrell Dow Pharmaceuticals Inc., Cincinnati, Ohio

[21] Appl. No.: 308,232

[22] Filed: Feb. 8, 1989

Related U.S. Application Data

[60] Continuation-in-part of Ser. No. 51,101, May 15, 1987, abandoned, which is a division of Ser. No. 807,613, Dec. 11, 1985, abandoned, which is a continuation-in-part of Ser. No. 792,359, Oct. 29, 1985, abandoned.

[51] Int. Cl.$^4$ ............................................. C07D 249/12
[52] U.S. Cl. ................................................. 548/263.2
[58] Field of Search ........................................ 548/263

[56] References Cited

U.S. PATENT DOCUMENTS 4,414,221  6/1983  Parsons et al. ...................... 548/262

FOREIGN PATENT DOCUMENTS 121432  11/1980  Japan .

OTHER PUBLICATIONS

S. Kuboda and M. Uda, *Chem. Pharm. Bull.*, 24(6), 1336-42 (1976).
G. Maffi, et al., *Il. Farmaco. Ed. Sci.*, 13, 629-38 (1958) (Translation provided).
Chem. Abst. 92:5718z, A. Ya. Lazaris, et al., *Izv. Akad. Nauk SSR, Ser. Khim*, 1979(8), 1870-3.
Chem. Abst. 77:164587n, T. Bany et al., *Rocz. Chem.* 46(6), 1123-8 (1972).
Chem. Abst. 69:67340d. T. Bany. Rocz. Chem., 42(2), 247-52 (1968).
J. P. Heinchart, et al., *Mol. Pharmacol.*, 20(3), 598-601 (1981).
J. P. Heinchart, et al, *Eur. J. Med. Chem.-Chim. Ther.*, 12(2), 117-2 (1977).
C. Guimon, et al. *Tetrahedron*, 32(22), 2769-74 (1975).
Tandon, et al., *Indian J. Chem.* 20B(11), 1017-8 (1981).
Chem. Abst. 86:170282m, M. Arbelot, et al. *Phosphorus Sulfur*, 1(2-3), 271-((1976).
W. A. Mosher, et al., *J. Heterocycl. Chem.* 8(2), 209-14 (1971).
K. C. Joshi, et al., *J. Indian Chem. Soc.*, 51(6), 613-5 (1974).
J. Daunis, et al., *Bull. Soc. Chim. Fr.*, 1972(4), 1511-20.
J. M. Kane. *Synthesis*(10), 912-9 (1987).
J. M. Kane, M. W. Dudley, S. M. Sorenson, and F. P. Miller *J. Med. Chem.* 31(6), 1253-8 (1988).

*Primary Examiner*—Glennon H. Hollrah
*Assistant Examiner*—Patricia L. Morris
*Attorney, Agent, or Firm*—Gary D. Street; Edlyn S. Simmons; Stephen L. Nesbitt

[57] ABSTRACT

This invention relates to novel 5-($R_n$-phenyl)-2,4-dialkyl-3H-1,2,4-triazole-3-thiones and to their use as antidepressants.

21 Claims, No Drawings

5-ARYL-2,4-DIALKYL-3H-1,2,4-TRIAZOLE-3-THIONES USEFUL AS ANTIDEPRESSANTS

BACKGROUND OF THE INVENTION

This is a continuation-in-part of application Ser. No. 51,101, filed May 15, 1987, now abandoned, which is a divisional of application Ser. No. 807,613, filed Dec. 11, 1985, now abandoned, which is a continuation-in-part of application Ser. No. 792,359, filed Oct. 29, 1985, now abandoned.

This invention relates to novel 5-aryl-2,4-dialkyl-3H-1,2,4-triazole-3-thiones, useful as antidepressants.

More specifically, this invention relates to compounds of the formula I and the pharmaceutically acceptable salts thereof wherein

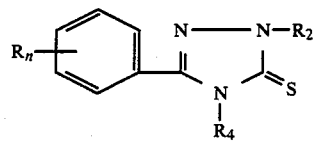

I

R represents halogeno, $C_{1-3}$ lower alkyl or $C_{1-3}$ lower alkoxy, with n being 1 or 2; and each of $R_2$ and $R_4$ independently represents $C_{1-3}$ lower alkyl.

For R, preferably halogeno represents chloro or fluoro, and methyl represents the preferred lower alkyl moiety. Lower alkoxy radicals include ethers having alkyl moieties paralleling the $C_{1-3}$ alkyl group. In formula I, n is one, representing a mono-substituted phenyl moiety with the R-substitutent being a group located at any of the ortho, meta or para positions, or n is 2, representing a disubstituted phenyl moiety wherein substitution is in any of the 2,3-; 2,4-; 2,5-; 2,6-; 3,4-; and 3,5-positions. Preferably $R_2$ and $R_4$ each represent methyl, but may independently represent any straight or branched $C_{1-3}$ alkyl group.

The pharmacological properties of these compounds and their relative potencies as antidepressants may readily be demonstrated by standard laboratory methodology. For example, the assay testing for prevention of reserpine-induced ptosis in mice and in rats is a standard assay. In this test, groups of weighed mice or rats are housed individually in wire mesh stick cages and administered test compound or vehicle. At a selected time thereafter, reserpine, prepared as a 4 mg/ml solution in dilute acetic acid, is given to rats at a dose of 4 mg/kg subcutaneously, and to mice as a 0.2 mg/ml solution in dilute acetic acid at a dose of 2 mg/kg intravenously into a tail vein. In each assay the animals are examined individually in a plexiglass cylinder 90 minutes later in the rat assay or 60 minutes after administration of reserpine to mice. Prevention or delay of ptosis is considered significant if the average closure of both eyes is less than 50% after observing for 30 seconds. The $ED_{50}$ for prevention of ptosis is defined as the dose of test compound that significantly prevents ptosis in 50% of the test animals.

In these tests imipramine has an $ED_{50}$ of 2.6 mg/kg (using a 30 minute pre-treatment time) in rats, while 5-(4-chlorophenyl)-2,4-dimethyl-3H-1,2,4-triazole-3-thione, one of the more potent examples of the compounds of this invention, has an $ED_{50}$ of 0.14 mg/kg under the same conditions. In mice, imipramine, at a 60 minute pretreatment time, has an $ED_{50}$ of 4.1 mg/kg while 5-(4-chlorophenyl)-2,4-dimethyl-3H-1,2,4-triazole-3-thione has an $ED_{50}$ of 0.27 mg/kg under the same conditions.

Antidepressant activity may also be assayed by testing for the antagonism of RO-4-1284-induced hypothermia according to the method of Carlos J. E. Niemegeers ("Antagonism of Reserpine-Like Activity", edited by S. Fielding and H. Lal, published by Futura, pg. 73–98). In this test, groups of male mice are weighed and housed individually in wire mesh stick cages. The rectal temperature of each mouse is recorded and the test compound or vehicle is then administered. At a selected time thereafter, RO-4-1284, prepared as a 2 mg/kg solution in distilled water, is administered at a dose of 20 mg/kg i.p. Mice are then placed in a cold room (36° F.) for 30 minutes, and then returned to room temperature for 30 minutes. At this time (60 minutes after RO-4-1284 administration) the rectal temperature of each mouse is again recorded. Under these conditions, RO-4-1284 causes a fall in rectal temperature of more than 6° C. The final temperatures of control groups of ten RO-4-1284-treated mice from a number of experiments are combined to form an "historic control" of 100 mice. This control is updated periodically by replacement of the oldest data. Any drug-treated animal which has final temperature (after RO-4-1284) which is greater than the mean+2 S.D. of the RO-4-1284 historic control is considered to exhibit significant antagonism to the hypothermic effect of RO-4-1284. The $ED_{50}$ for antagonism is defined as that dose of test compound which significantly antagonizes RO-4-1284 hypothermia in 50% of the test animals.

Using a 60 minute pretreatment time and these criteria for evaluation of effects, desipramine was found to have an $ED_{50}$ of 0.1 mg/kg i.p.; imipramine, an $ED_{50}$ of 1.8 mg/kg i.p., Catron ®, an $ED_{50}$ of 0.7 mg/kg i.p., and 5-(2,6-difluorophenyl)-2,4-dimethyl-3H-1,2,4-triazole-3-thione an $ED_{50}$ of 0.44 mg/kg i.p.

These standard laboratory tests demonstrate that the compounds of this invention have pharmacological effects generally attributed to antidepressants and thus the compounds of this invention will elevate mood in patients suffering from depression and will have an end-use application in the treatment of patients suffering from endogenous depression, a term used interchangeably with psychotic or involutional depression. In this use, the compound (I) will exert a relatively quick onset of action and have a prolonged duration of activity. The dosage regimen may readily be ascertained by those of ordinary skill in the art by comparison with other agents clinically known to be useful as antidepressants. In general, the compounds may be expected to exert their antidepressant effects at dose levels of about 0.25–25 mg/kg of body weight per day although, of course, the degree of severity of the disease state, age of the patient and other factors determined by the attending diagnostician will influence the exact course and dosage regimen suitable for each patient. In general the parenterally administered doses are about ¼ to ½ that of the orally administered dose.

For oral administration, the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment, the compounds of general formula I can be tableted with conventional tablet bases such as lactose, sucrose and cornstarch, in combination with binders, such as acacia, cornstarch or gelatin, disintegrating agents such as potato starch or alginic acid, and a lubricant such as stearic acid or magnesium stearate.

For parenteral administration, the compounds may be administered as injectable dosages of a solution or suspension of the compound in a physiologically acceptable diluent with a pharmaceutical carrier which can be a sterile liquid such as water, alcohols, oils and other acceptable organic solvents, with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol, or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert material such as biodegradable polymers or synthetic silicones, for example Silastic®, a silicone rubber manufactured by the Dow-Corning Corporation.

As is true in many classes of compounds generally suitable for any particular pharmacological activity having a therapeutic end-use application, certain subgeneric groups and certain specific members of the class are preferred because of their overall therapeutic index, biochemical and pharmacological profile. In this instance the preferred compounds are those wherein both $R_2$ and $R_4$ groups are methyl, those wherein the R substituent is chloro or fluoro, those wherein the $R_n$ substituent is a monochloro or monofluoro substituent, and those wherein $R_n$ represents dichloro or difluoro substitution preferably at the 2,4-, 3,4- or 2,6-positions. Specifically preferred compounds are:

5-(4-chlorophenyl)-2,4-dimethyl-3H-1,2,4-triazole-3-thione
5-(4-fluorophenyl)-2,4-dimethyl-3H-1,2,4-triazole-3-thione
5-(2-fluorophenyl)-2,4-dimethyl-3H-1,2,4-triazole-3-thione
5-(2,6-difluorophenyl)-2,4-dimethyl-3H-1,2,4-triazole-3-thione
5-(3-fluorophenyl)-2,4-dimethyl-3H-1,2,4-triazole-3-thione
5-(4-methylphenyl)-2,4-dimethyl-3H-1,2,4-triazole-3-thione
5-(2,4-difluorophenyl)-2,4-dimethyl-3H-1,2,4-triazole-3-thione
5-(2-chlorophenyl)-2,4-dimethyl-3H-1,2,4-triazole-3-thione
5-(4-methoxyphenyl)-2,4-dimethyl-3H-1,2,4-triazole-3-thione The compounds of formula I may readily be prepared using processes and procedures analogously known in the art as seen by the following reaction scheme.

REACTION SCHEME

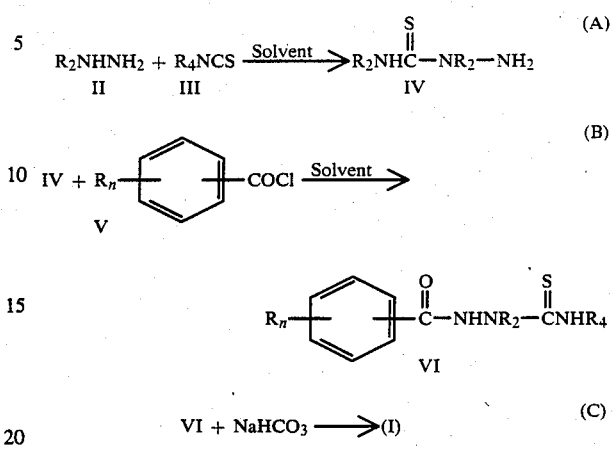

wherein $R_2$, $R_4$, n and R are as previously defined.

In step A, the preparation of the thiosemicarbazides (IV) is readily effected by reacting hydrazine (II) with an isothiocyanate (III) by contacting the reactants in a suitable solvent. The reaction is quite rapid and may be carried out at 0° C. to room temperature. Although the reaction proceeds rapidly, the mixture may be left for up to 24 hours without significant decrease in yields. Reflux conditions may be employed but are not preferred. Almost all solvents (with the exception of water and organic acids) may be used. Anhydrous alcohols (preferably ethanol or methanol) are preferred although DMF, CHCl₃, CH₂Cl₂, THF and Et₂O may also be used. The required hydrazines and isothiocyanates are usually commercially available, but may be prepared by known techniques quite obvious to one of ordinary skill in the art.

In Step B, the desired substituted benzoyl thiosemicarbazides (VI) may be prepared by reacting the thiosemicarbazides (IV) with an $R_n$-substituted benzoyl chloride (V) in an aprotic solvent such as pyridine, CHCl₃, THF and the like. The acylation proceeds rather easily at temperatures ranging from 0° C. to room temperature over periods of 3 to 24 hours, although elevated temperatures (e.g. reflux temperatures) may be employed. Again, the acid halides (V) generally are commercially available but may also be prepared from the corresponding acids which are available from obvious starting materials.

In Step C, the substituted benzoyl thiosemicarbazides (VI) are subjected to a cyclization reaction which is effected by heating the compounds (VI) in an aqueous base, e.g. sodium bicarbonate or sodium hydroxide. Alcoholic bases may be utilized, but generally are less desirable. The reaction is conducted at about the reflux temperature of the solvent, preferably at about 65°-100° C. In practice, the thiosemicarbazides (VI) need not be purified for use in Step C so that even 1:1 mixtures with pyridine hydrochloride, produced as a by-product when pyridine is employed as a solvent in Step B, may be used.

The following specific examples are given to illustrate the preparation of the compounds of this invention although the scope of compounds exemplified is not meant to be limiting.

Preparation of $R_2,R_4$-Substituted-Thiosemicarbazides

EXAMPLE 1

2,4-Dimethylthiosemicarbazide

To a stirred solution of methyl hydrazine (16.0 ml, $3.00 \times 10^{-1}$ mole) and sieve dry ethanol (50 ml) was added dropwise a solution of methyl isothiocyanate (22.0 g, $3.00 \times 10^{-1}$ mole) and sieve dry ethanol (30 ml). The reaction was exothermic and gently refluxed as the isothiocyanate was added. A precipitate soon formed. After stirring overnight, the reaction was cooled in an ice bath. The precipitate was then collected by filtration, washed with a little cold isopropanol, and dried by suction, affording a colorless solid: 26.7 g (75%). This material was crystallized two times from water and two times from isopropanol, affording small colorless needles: 14.7 g (41%), mp 135°–137° C.

Preparation of 1-($R_n$-Benzoyl)-$R_2$, $R_4$, -Substituted Thiosemicarbazides

EXAMPLE 2

1-(4-Chlorobenzoyl)-2,4-dimethylthiosemicarbazide

To a stirred solution of 2,4-dimethylthiosemicarbazide (1.19 g, $1.00 \times 10^{-2}$ mole) and pyridine (10 ml) was added dropwise 4-chlorobenzoyl chloride (1.3 ml, $1.02 \times 10^{-2}$ mole). The reaction turns yellow and a mild exotherm is noted. After stirring overnight the reaction was evaporated to dryness affording a beige solid: 3.61 g (97%) which represents a mixture of the desired 1-(4-chlorobenzoyl)-2,4-dimethylthiosemicarbazide and pyridine hydrochloride. In general this mixture was used without further purification in the subsequent cyclization step. If pure 1-(4-chlorobenzoyl)-2,4-dimethylthiosemicarbazide is desired, the above mixture is treated with water and that which does not dissolve is collected by filtration. After drying by suction this material is crystallized from ethanol affording colorless matted needles: 1.03 g (40%), mp=206°–208° C. (decomp).

Preparation of Final Products

EXAMPLE 3

5-(4-Chlorophenyl)-2,4-dimethyl-3H-1,2,4-triazole-3-thione

The 1:1 mixture of 1-(4-chlorobenzoyl)-2,4-dimethylthiosemicarbazide and pyridine hydrochloride (3.61 g of mixture) from Example 2 and 1 molar aqueous NaHCO3 (100 ml, $1.00 \times 10^{-1}$ mole) were stirred and warmed to reflux. After refluxing for 5 hours the reaction was allowed to cool. It was then placed in a refrigerator for several hours before the precipitate was collected by filtration. The collected material was dried partially by suction before being transferred to a desiccator where it was dried at high vacuum. This affords the desired product as a beige powder: 2.01 g (84%). This was purified by flash chromatography and subsequent crystallization from isopropanol yielding small, slightly yellowish plates: 1.74 g (73%), mp 113°–115° C.

In a similar manner, by substituting a variety of substituted benzoyl chlorides and a variety of 2,4-disubstituted thiosemicarbazides for the reactants of examples 1-3 and by substantially following the techniques therein, the following compounds are readily prepared.

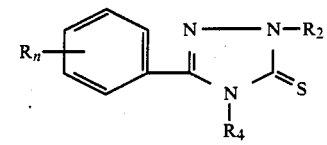

| $R_n$ | $R_2$ | $R_4$ | M.P. °C. |
| --- | --- | --- | --- |
| 4-Cl | $CH_3$ | $C_2H_5$ | 113–115° |
| 4-F | $CH_3$ | $CH_3$ | 130–132° |
| 4-Cl | $C_2H_5$ | $CH_3$ | 118–120° |
| 4-Cl | $C_2H_5$ | $C_2H_5$ | 91–93° |
| 2-Cl | $CH_3$ | $CH_3$ | 138–140° |
| 4-Cl | $CH_3$ | $CH_3$ | 114–116° |
| 4-Cl | $CH_3$ | $n-C_3H_7$ | 240–250°/0.55 mm Hg |
| 2,4-$Cl_2$ | $CH_3$ | $CH_3$ | 135–137° |
| 3,4-$Cl_2$ | $CH_3$ | $CH_3$ | 161–163° |
| 2,6-$Cl_2$ | $CH_3$ | $CH_3$ | 115–116° |
| 2-F | $CH_3$ | $CH_3$ | 106–108° |
| 3-F | $CH_3$ | $CH_3$ | 126–128° |
| 2,4-$F_2$ | $CH_3$ | $CH_3$ | 102–104° |
| 2,6-$F_2$ | $CH_3$ | $CH_3$ | 158–160° |
| 4-$CH_3$ | $CH_3$ | $CH_3$ | 94–96° |
| 4-$CH_3O$ | $CH_3$ | $CH_3$ | 96–98° |

What is claimed is:

1. A compound of the formula

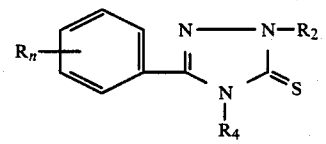

wherein
R is halogen, $C_{1-3}$ lower alkyl or $C_{1-3}$ lower alkoxy,
n is 1 or 2, and
$R_2$ and $R_4$ independently represent $C_{1-3}$ lower alkyl.

2. A compound of claim 1 wherein R is halogeno.
3. A compound of claim 2 wherein n is one.
4. A compound of claim 2 wherein n is two.
5. A compound of claim 1 wherein $R_2$ and $R_4$ each are methyl.
6. A compound of claim 5 wherein R is $C_{1-3}$ alkyl and n is one.
7. A compound of claim 5 wherein R is fluoro and n is one.
8. A compound of claim 5 wherein R is fluoro and n is two.
9. A compound of claim 5 wherein R is chloro and n is one.
10. A compound of claim 5 wherein R is chloro and n is two.
11. A compund of claim 5 wherein R is $C_{1-3}$ alkoxy and n is one.
12. A compound of claim 7, said compound being 5-(3-fluorophenyl)-2,4-dimethyl-3H-1,2,4-triazole-3-thione.
13. A compound of claim 7, said compound being 5-(4-fluorophenyl)-2,4-dimethyl-3H-1,2,4-triazole-3-thione.
14. A compound of claim 7, said compound being 5-(2-fluorophenyl)-2,4-dimethyl-3H-1,2,4-triazole-3-thione.
15. A compound of claim 8, said compound being 5-(2,6-difluorophenyl)-2,4-dimethyl-3H-1,2,4-triazole-3-thione.

16. A compound of claim 8, said compound being 5-(2,4-difluorophenyl)-2,4-dimethyl-3H-1,2,4-triazole-3-thione.

17. A compound of claim 9, said compound being 5-(4-chlorophenyl)-2,4-dimethyl-3H-1,2,4-triazole-3-thione.

18. A compound of claim 9, said compound being 5-(2-chlorophenyl)-2,4-dimethyl-3H-1,2,4-triazole-3-thione.

19. A compound of claim 10, said compound being 5-(3,4-dichlorophenyl)-2,4-dimethyl-3H-1,2,4-triazole-3-thione.

20. A compound of claim 6, said compound being 5-(4-methylphenyl)-2,4-dimethyl-3H-1,2,4-triazole-3-thione.

21. A compound of claim 11, said compound being 5-(4-methoxyphenyl)-2,4-dimethyl-3H-1,2,4-triazole-3-thione.

* * * * *